United States Patent
Krespan

[11] 3,952,015
[45] Apr. 20, 1976

[54] MACROCYCLIC COMPOUNDS HAVING OXA AND AZA LINKAGES IN THE RING AND CONTAINING SPIROOXETANE GROUPS

[76] Inventor: Carl George Krespan, 2705 Point Breeze Drive, Barkley, Wilmington, Del. 19810

[22] Filed: Aug. 9, 1974

[21] Appl. No.: 497,050

Related U.S. Application Data

[63] Continuation-in-part of Ser. No. 415,249, Nov. 12, 1973; abandoned.

[52] U.S. Cl............................... 260/338; 260/333; 260/239 B; 260/239 BC; 260/438.1
[51] Int. Cl.².............. C07D 493/10; C07D 498/10
[58] Field of Search..................................... 260/338

[56] References Cited
UNITED STATES PATENTS
3,763,188  10/1973  Krespan............................. 260/338

Primary Examiner—Norma S. Milestone

[57] ABSTRACT

Compound having the formula

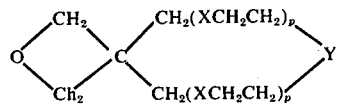

wherein Y is $-XCH_2CH_2-X-$, $-X(CH_2CH_2X)_2$ or

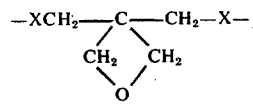

$p$ is 1 to 4, and each X is O or NH, N-alkanoyl, N-benzoyl wherein the benzene ring is optionally substituted with $-NO_2$, $-NH_2$, or $-CH_3$, N-alkyl or N-$\beta$-hydroxyalkyl each of up to 8 carbons and wherein the total number of N is 1 to 3 are disclosed. The compounds can be polymerized by opening of the oxetane ring in the presence of electrophilic agents, or the oxetane ring can be hydrolyzed to a dihydroxy group and reacted with diacid halides to form polyesters or with diisocyanates to form polyurethanes. Both monomers and polymers complex metal ions and can be used to separate such ions from solutions.

6 Claims, No Drawings

MACROCYCLIC COMPOUNDS HAVING OXA AND AZA LINKAGES IN THE RING AND CONTAINING SPIROOXETANE GROUPS

RELATED APPLICATION

This application is a continuation-in-part of U.S. Ser. No. 415,249 filed Nov. 12, 1973, and now abandoned.

1. Field of the Invention

This invention relates to polymerizable macrocyclic compounds containing 1 to 3 aza substituents and oxa substituents.

2. The Prior Art

The preparation of 3,3,-disubstituted oxacyclobutanes (oxetanes by preferred nomenclature) and their polymerization by electrophilic catalysts such as boron fluoride has been described by A. C. Farthing, J. Chem. Soc. 3648 (1955).

The reaction of the sodium salt of guaiacol with the tetra(para toluene sulfonate) derivatives of pentaerythritol in dimethyl sulfoxide has been reported to produce cyclic polyethers some of which contain spirooxetane rings by A. W. Archer and P. A. Claret Chem. & Ind. 1271 (1969).

C. J. Pedersen, J. Am. Chem. Soc. 89 7017 (1967) has described cyclic polyethers known as crown compounds which are capable of complexing cations, especially alkali metals.

B. Dietrich et al., Tetrahedron Letters, No. 34 2885 (1969), have described the preparation of macrocyclic polyethers containing two nitrogen atoms in the ring.

SUMMARY OF THE INVENTION

The compounds of the present invention have the formula:

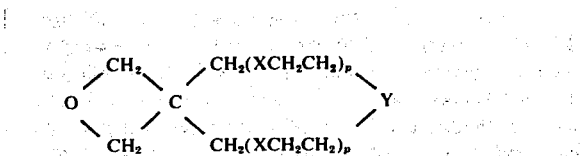

where Y is —XCH$_2$CH$_2$—X—, —X(CH$_2$CH$_2$X)$_2$— or

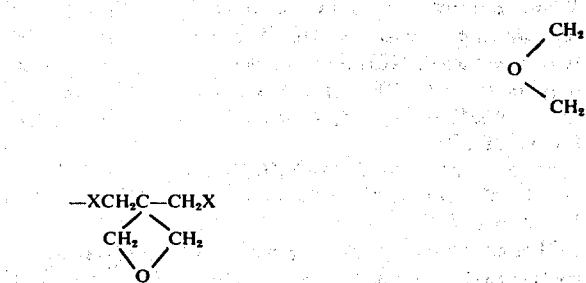

$p$ is 1 to 4, and each X separately is O, NH, N-alkanoyl, N-benzoyl where the benzene ring is optionally substituted with —NO$_2$, —NH$_2$ or —CH$_3$; N-alkyl, or N-β-hydroxyalkyl each of up to 8 carbon atoms with the proviso that the number of nitrogen atoms is from 1 to 3.

DETAILED DESCRIPTION OF THE INVENTION

The present invention is directed to macrocyclic compounds containing both oxa and aza linkages in the macrocyclic ring and also containing 1 or 2 spirocyclic oxetane rings. The presence of the nitrogen atoms in the ring enhances the complexing ability of the compound with heavy metal ions while the presence of the spirocyclic oxetane rings provide the capability for polymerization either directly by catalysis with electrophilic catalysts which open the oxetane rings, or indirectly by hydrolysis of each oxetane ring to a diol followed by reaction with diacid halide to form polyester, or with diisocyanates to form polyurethanes or the like.

In preferred compositions only simple oxa or aza (—NH—) linkages are present and the number of ring heteroatoms is 5–6, i.e., $p = 1$ in the generic formula examples are:

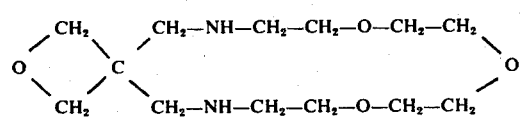

2,9,12,15-tetraoxa-6,18-diazaspiro[3.15]nonadecane

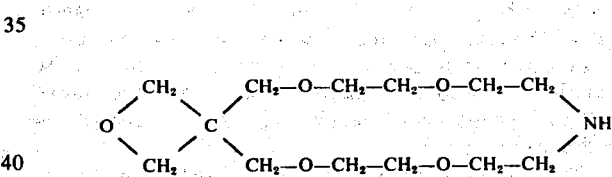

2,6,9,15,18-Pentaoxa-12-azaspiro[3,15]nonadecane

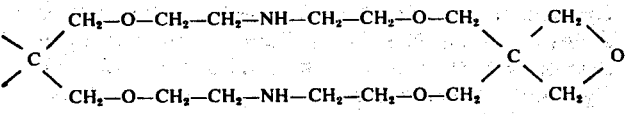

2,6,12,16,19,25-Hexaoxa-9,22-diazadispiro [3.9.3.9] hexacosane

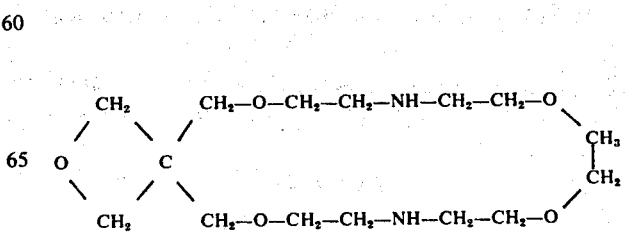

2,6,12,15,21-Pentaoxa-9,18-diazaspiro[3.18]docosane

The spirooxetanes of this invention are prepared by reaction of 3,3-bis(chloromethyl)oxetane or 3,3-bis-(bromomethyl)oxetane with an aminoether in a polar, non-interfering solvent such as t-butanol, dimethylformamide, or tetrahydrofuran. The aminoether is terminated at each end by hydroxyl or amine groups. To the extent that the aminoether component has hydroxyl end-groups a base such as potassium t-butoxide or sodium hydride must be used to convert the hydroxyl to a reactive alkoxide. Bases such as sodium hydroxide and potassium hydroxide can also be used with only a small lowering of yield.

It is preferred to conduct the reaction at temperatures of 50°–100°C at 1 atm pressure for 1–24 hours. The temperature may vary, however, between 25°–100°C. If a pressure vessel is used, the pressure can be above 1 atm. Reaction times, depending on the temperature, may vary from a few minutes to a week.

The amine groups of the spirooxetanes can react with acid halides such as acetyl chloride, benzoyl chloride, p-nitrobenzoyl chloride, p-methylbenzoyl chloride and the like to yield alkanoyl derivative or benzoyl derivatives which may be substituted with alkyl, or nitro groups. The nitro groups can be catalytically reduced with hydrogen to yield aminobenzoyl compounds. Alkyl halides, particularly when the halogen is chlorine, bromine or iodine can be employed to alkylate the amino groups to form alkyl derivatives. The reaction of alkene epoxides with the amino groups gives β-hydroxy alkyl derivatives.

The products of this invention are isolated from their reaction mixtures by standard procedures of filtration, distillation, crystallization and extraction.

UTILITY

The monomeric azapolyoxasubstituted macrocyclic compounds of the invention find generic utility in their ability to complex metal ions. Their particular ability to complex with the heavier metals such as $Cu^{++}$, $Ag^{+}$ and $Hg^{++}$ and transition metals such as $Ni^{++}$, $Co^{++}$ and $Pd^{++}$ is a distinction and advantage over the macrocyclic polyethers. These compounds may also be employed as monomers in cationic polymerizations to yield polymers which are capable of complexing metal ions.

SPECIFIC EMBODIMENTS OF THE INVENTION

The following examples are intended to illustrate this invention, but not to fully delineate the scope thereof.

EXAMPLE 1

2,9,12,15-Tetraoxa-6,18-diazospiro[3.15]nonadecane

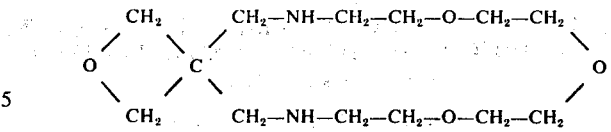

A mixture of 15.5 g (0.10 mol) of 3,3-bis(chloromethyl)oxetane, 19.2 g (0.10 mol) of 1,11-diamino-3,6,9-trioxaundecane, 38.7 g (0.30 mol) of diisopropylethylamine, and 500 ml of n-propanol was refluxed under nitrogen for 3 days. The mixture was cooled, treated with 21.2 g (0.20 mol) of anhydrous sodium carbonate, and refluxed an additional 5 hrs. The reaction mixture was then filtered and distilled in a molecular still to give 4.6 g (17%) of an approximately equimolar mixture of the isomers 2,9,12,15-tetraoxa-6,18-diazaspiro[3.15]nonadecane and

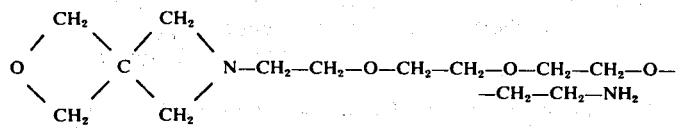

N-(11-amino-3,6,9-trioxaundecyl)-2-oxa-6-azaspiro[3,3]heptane. bp 108°–110° (0.1 μ). Ir 2.98 (sh) and 3.02 (NH), 6.26 ($NH_2$ rel weak), 8.9 (broad COC), 10.28 and 10.61 μ (oxetane ring); nmr indicated a mixture of oxetanes for which assignments could be made as described below.

Anal. Calcd for $C_{13}H_{26}N_2O_4$: C, 56.91; H, 9.55; N, 10.21; M.W., 274. Found: C, 56.92; H, 9.16; N, 9.88; 56.88 9.23 9.93; M.W. 274 (field ionization mass spec).

The mixture of isomers was separated by isolation of 2,9,12,15-tetraoxa-6,18-diazaspiro[3.15]nonadecane as the crystalline complex with NaSCN. A solution of 1.2 g (0.0044 mol) of the mixture and 0.32 g (0.004 mol) of NaSCN in 10 ml of acetone was evaporated to ca 5 ml, 5 ml of ether was added and the mixture was allowed to stand overnight. The supernatant liquid was decanted and the solid recrystallized from acetone/ether, then from acetone to give the 1:1 complex as large colorless cubes, mp 154.5°–155.5°. Ir (Nujol) 3.08 (HN), 4.85, (SCN), 8.8–9.5 (COC), 10.21 and 10.60 μ (oxetane); nmr (acetone-$d_6$) $^1H$ 4.43 (s, 2H oxetane $CH_2$), 3.67 (s, 4H, $OCH_2CH_2O$), 3.12 (s, 2H, $C-CH_2N$), and 2.43 ppm (broad, 1H, NH) with rough triplets of an AA′BB′: pattern at 225, 220.5 (hidden), 216 Hz (2H, $NCH_2CH_2O$) and 177, 172.5, 168 Hz (2H, $NCH_2CH_2O$).

Anal. Calcd. for $C_{14}H_{25}N_3NaO_4S$: C, 47.31; H, 7.37; N, 11.82; Na, 6.47. Found: C, 47.49; H, 7.21; N, 11.62; Na, 7.33.

The mother liquid from complex formation was evaporated to a viscous residue and the residue extracted with 50 ml of benzene. Evaporation of the benzene gave a residue which was extracted with 50 ml of pet ether. Evaporation of the pet ether gave an oil, nearly pure N(11-amino-3,6,9-trioxaundecyl)-2-oxa-6-oxaspiro[3,3]-heptane. Nmr (acetone-$d_6$) $^1H$ 4.60 (s, 2H, oxetane), 3.57 and 3.54 (both s, combined with 6H, $NCH_2CH_2$ $OCH_2CH_2OCH_2CH_2$), and 3.31 ppm (s, 2H acetidine) with rough triplets of an AA′BB′ pattern hidden near 200 Hz and at 155.5, 150, and 144 Hz; $NH_2$ resonance uncertain due to impurity peaks.

EXAMPLE 2

2,6,9,15,18-Pentaoxa-12-azaspiro[3.15]nonadecane

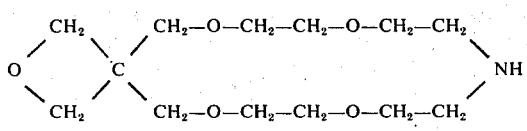

Preparation of the required 3,9-dioxa-6-azaundecan-1,11-diol was carried out as follows:

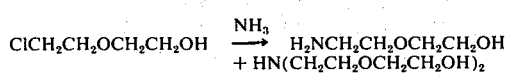

A mixture of 450 g (3.6 mol) of 2-(2-chloroethoxy)-ethanol, 400 g of ammonia and 2 l. of absolute ethenol was heated at 125° for 15 hours under autogenous pressure in a 3-gallon autoclave. The dark reaction mixture was refluxed for 4 hours with 600 g of anhydrous $Na_2CO_3$, filtered and distilled to give 16.4 g (43%) of 1-amino-3-oxapentane-5-ol, bp 60°–65° (0.2 mm), and 145.3 g (42%) of 3,9-dioxa-6-aza-undecan-1,11-diol, bp 140°–145° (15μ).

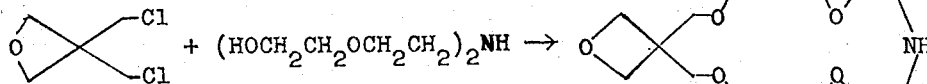

A solution of 62.0 g (0.40 mol) of bis(chloromethyl)oxetane, 94.0 g (0.84 mol) of potassium butoxide, and 77.2 g (0.40 mol) of 3,9-dioxa-6-aza-undecan-1,11-diol in 1 l. of t-butanol was refluxed and stirred under $N_2$ for 6 days. Filtration and evaporation of the reaction mixture to 50° (0.5 mm) gave a residue which crystallized on cooling. The crude 2,6,9,15,18-pentaoxa-12-azaspiro-[3.15]-nonadecane was kept molten at 90° and extracted continuously with heptane for 1 day. The cooled extract was filtered, and solid so isolated was recrystallized from ether to give 74.2 g (67%) of product mp 79°–81°. An analytical sample, mp 80°–81°, was recrystallized from ether. Ir (Nujol): 3.01 (NH), 8.6–9.1 (COC), 10.22 and 10.74 μ (ocetane). Nmr ((CD$_3$)$_2$CO): 4.32 (singlet, 4, oxetane CH$_2$), 3.65(singlet, 4, C-CH$_2$O), 3.57 (singlet, 12 with underlying OCH$_2$CH$_2$N, OCH$_2$CH$_2$) and 2.32 ppm (broad singlet, 1, NH) with OCH$_2$CH$_2$N appearing as A$_2$B$_2$ at 214 (hidden), 209, and 204 Hz (OCH$_2$) and 162, 157, and 152 Hz (4, CH$_2$N). Addition of D$_2$O moved the NH resonance downfield.

Anal. Calcd for C$_{13}$H$_{25}$NO$_5$: C, 56.71; H, 9.15; N, 5.09; mol wt, 275. Found: C, 56.61; H, 8.88; N, 5.04; mol wt, 272 (cry. φH)

A 1:1 complex of this macrocycle with NaSCN was prepared in acetone, crystallized by concentration and addition of a small amount of ether and isolated in 93% yield, mp 113°–114°. A recrystallized sample had mp 113°–114°. Ir (Nujol): 3.03 (NH), 4.86 (SCN), 8.7–9.5 (COC), 10.36, 10.57 and 10.75 μ (oxetane). Nmr (CD$_3$)$_2$CO: 4.43 (singlet, 4, oxetane CH$_2$, 3.98 (singlet, 4, C-CH$_2$O), and 3.73 (singlet, 12 with nearby OCH$_2$CH$_2$N, OCH$_2$CH$_2$O), with OCH$_2$CH$_2$N appearing as A$_2$B$_2$ at 221, 216.5 and 211.5 Hz (OCH$_2$) and 174.5, 169.5, and 165 Hz (4, CH$_2$N).

Anal. Calcd for C$_{14}$H$_{25}$N$_2$NaO$_5$S: C, 47.18; H, 7.07; N, 7.85; Na, 6.45. Found: C, 47.41; H, 7.14, N, 8.16; Na, 6.06.

a. Alkylation of 2,6,9,12,18-Pentaoxa-12-azaspiro[3.15]-nonadecane

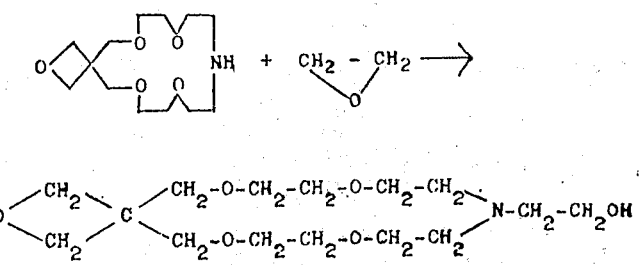

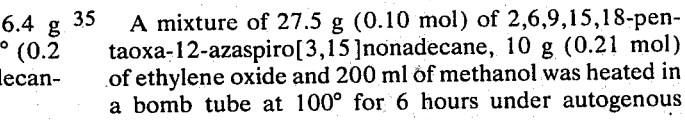

A mixture of 27.5 g (0.10 mol) of 2,6,9,15,18-pentaoxa-12-azaspiro[3,15]nonadecane, 10 g (0.21 mol) of ethylene oxide and 200 ml of methanol was heated in a bomb tube at 100° for 6 hours under autogenous pressure. Solvent was evaporated, and the product was volatilized in a very short path still at 190° (~20 μ), giving 27.6 g (87%) of N-hydroxyethyl-2,6,9,15,18-pentaoxa-12-azaspiro[3.15]nonadecane as a nearly colorless oil. Ir: 2.90 (OH), 8.7–9.5 (COC, COH), 10.23 and 10.80 μ oxetane). Nmr ((CD$_3$)$_2$CO): 4.29 (singlet, 4, oxetane CH$_2$), 3.74 (singlet, 4, C-CH$_2$O), 3.6–3.3 (multiplet, 15, OCH$_2$CH$_2$O + OH + OCH$_2$CH$_2$N), 2.85–2.5 ppm (multiplet, 6, CH$_2$N).

Anal. Calcd for C$_{15}$H$_{29}$NO$_6$: C, 56.41; H, 9.15; N, 4.39. Found: C, 56.43; H, 8.80; N, 4.54.

b.

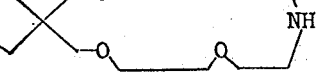

12-(4'-Nitrobenzoyl)-2,6,9,15,18-pentaoxa-12-azaspiro-[3.15]nonadecane

A solution of 1.86 g of p-nitrobenzoyl chloride and 2.75 g of 2,6,9,15,18-pentaoxaspiro[3.15]nonadecane in 50 ml of benzene was treated with small portions of a solution of 1.10 g of triethylamine in benzene over a period of 5 minutes. The solution became cloudy and fine crystals deposited. After 2 hr the mixture was shaken with two 30 ml portions of water. The benzene layer was separated and dried (MgSO$_4$). Solvent was stripped under reduced pressure and the resulting colorless oil was analyzed. It did not crystallize and appeared to retain some solvent.

| Anal. Calcd for C$_{20}$H$_{28}$N$_2$O$_8$: | C, | 56.59; | H, | 6.65; | N, | 6.60 |
|---|---|---|---|---|---|---|
| Found: | C, | 58.23; | H, | 6.80; | N, | 5.59 |
|  |  | 58.64 |  | 6.89 |  | 5.73 |
|  |  | 58.05 |  |  |  |  |

Nmr spectrum- δ 7.67 [4H] quartet (aromatic), δ 4.40 [4H] singlet (oxetane CH$_2$), δ 2.80 [4H] (spiro CH$_2$), δ 3.63 [16H] broad (OCH$_2$ and NCH$_2$ of macrocyclic ring). This agrees well with the assigned structure.

c. 12-(4'-Aminobenzoyl)-2,6,9,15,18-pentaoxa-12-azaspiro-[3.15]nonadecane

A solution of the nitro compound above in 100 ml of ethanol was hydrogenated on a Parr shaking apparatus using 10% palladium on charcoal catalyst. The mixture was filtered, and solvent was remove under reduced pressure. The resulting colorless oil (3.276 g) crystallized on standing to form a mass of silky needles. A 2.866 g portion was recrystallized from 25 ml of benzene to yield 1.78 g of white crystals which melted at 114.5°–117.5°.

| Anal. Calcd for C$_{20}$H$_{30}$N$_2$O$_6$: | C, | 60.89; | H, | 7.67; | N, | 7.10 |
|---|---|---|---|---|---|---|
| Found: | C, | 59.56; | H, | 7.57; | N, | 6.63 |
|  |  | 59.78 |  | 7.60 |  | 7.00 | d. Polymerization of N-hydroxyethyl-2,6,9,15,18-pentaoxa-12-azaspiro[3.15]nonadecane Treatment of N-hydroxyethyl-2,6,9,15,18-pentaoxa-12-azaspiro[3.15]nonadecane with a slight excess of CF$_3$SO$_3$H over that required to neutralize the amine group led to polymer formation, as follows:

A solution of 18.5 g (0.058 mole) of N-hydroxyethyl-2,6,9,15,18-pentaoxa-12-azaspiro[3.15]nonadecane and 9.3 g (0.062 mol) of CF$_3$SO$_3$H in 300 ml of glyme had pH ~6. Addition of a small amount of CF$_3$SO$_3$H did not increase pH, indicating rapid addition to the oxetane ring. The homogeneous solution was allowed to stand for 4 days at 25°, when two phases were present. Nmr showed oxetane to be nearly all reacted. After an additional 2 days at 25°, 2.6 g (0.035 mol) of lithium carbonate was added, and the mixture was refluxed for 3 hr. The lower layer was extracted with 50 ml of glyme, and the combined upper layer and glyme extract evaporated to give 24.8 g of glassy residue. Distillation at 160°–175° (0.05 mm) for 2 weeks removed only 1.6 g of oil; the residue was a hard glass which was insoluble in hot water.

e. Addition of Hydroxylic Compounds to Oxetane Ring of 2,6,9,15,18-Pentaoxa-12-azaspiro[3.15]nonadecane The oxetane ring in 2,6,9,15,18-pentaoxa-12-azaspiro[3.15]nonadecane was shown to add hydroxylic compounds by acid-catalyzed reaction with 2-chloroethanol to give 1-hydroxymethyl-1-(4-chloro-2-oxabutyl)-2,5,11,14-tetraoxa-8-azacyclopentadecane.

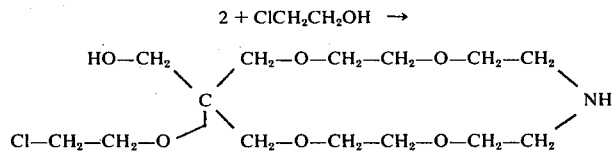

A solution of 27.5 g (0.10 mol) of the nonadecane and 7.9 g (in 400 ml of conc. H$_2$SO$_4$) of 2-chloroethanol was heated at 100° for 3½ days, after which time the nmr spectrum of an aliquot detected no oxetane ring. Solvent was evaporated, 900 ml of water added, and another 250 ml of distillate taken. The resulting solution was treated with 24.4 g of Ba(OH)$_2$·8H$_2$O, then carbonated to pH = 9 and filtered. The filtrate was diluted to 2500 ml with water, refluxed under N$_2$ for 3 days and evaporated to give 46 g of viscous residue. Product was acidic, indicating sulfate esters not completely solvolyzed, so the residue was dissolved in water, 40 g of BaCO$_3$ added and the mixture refluxed 2 hr. Isolation of the organic product and volatilization in a short-path still at 140°–145° (0.03 mm) gave 9.7 g (29%) of crude product. Mass spec (disilylated derivative): m/e 499 (M$^+$), 484 (M$^+$-CH$_3$), 450 (M$^+$-CH$_2$Cl); empirical formula established as C$_{21}$H$_{46}$NO$_6$ClSi$_2$ by high resol. mass spec.

EXAMPLE 3

2,6,12,16,19,25-Hexaoxa-9,22-diazadispiro[3.9.3.9-]hexacosane

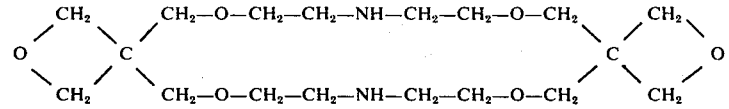

A solution of 105.0 g (1.0 mol) of diethanolamine, 155.0 g (1.0 mol) of 3,3-bis(chloromethyl)oxetane, and 233 g (2.08 mol) of potassium t-butoxide in 2.5 l. of t-butanol was refluxed and stirred under N$_2$ for 2 days. The addition of oxetane, glycol, and butoxide was repeated, and reaction continued for 4 days. Filtration and evaporation of the filtrate to 60° (0.5 mm) gave a semisolid residue which was kept at 90° and extracted continuously with heptane for 3 days. Removal of heptane from the extract and recrystallization from ether gave 63.6 g (17%) of 2,6,12,16,19,25-hexaoxa-9.22-diazadispiro[3.9.3.9]hexacosane, mp 118.5°–119°. An analytical sample was recrystallized from tetrahydrofuran, mp 118.5°–119°. Ir (Nujol): 3.04 (NH), 8.6–9.5

(COC), 10.07, 10.29, 10.52 and 10.75 μ (oxetane). Nmr ((CD$_3$)$_2$CO): 4.36 (singlet, 1, oxetane CH$_2$), 3.68 (singlet, 2 along with underlying OCH$_2$CH$_2$N, CCH$_2$O), 2.30 ppm (very broad NH) with A$_2$B$_2$ branches at 221 (hidden), 216.5 and 211 Hz (OCH$_2$CH$_2$N) and 172, 166.5 and 162 Hz (OCH$_2$CH$_2$N).

Anal. Calcd for C$_{18}$H$_{34}$N$_2$O$_6$: C, 57.73; H, 9.15; N, 7.48; mol wt, 374.5. Found: C, 57.62; H, 8.86; N, 7.61; mol wt, 398 (ebul ϕH).

a. Formation of Stable Complex of 2,6,12,16,19,25-Hexaoxa-9,22-diazadispiro[3.9.3.9-]hexacosane The presence of nitrogen in the macro rings of these products extends their ability to form stable complexes to ions of heavy metals such as copper and silver, as well as transition metals. For example, 2,6,12,16,19,25-hexaoxa-9,22-diazadispiro[3.9.3.9-]hexacosane gives a 1:1 complex with cupric acetate.

A solution of 0.36 g (0.001 mol) of 8 and 0.20 g (0.001 mol) of Cu(OAc)$_2$.H$_2$O in 25 ml of absolute ethanol was deep blue in color. Removal of nearly all the ethanol and addition of 25 ml of ether gave 0.52 g (93%) of violet 1:1 complex, mp 156°–158° (dec). Recrystallization from ether/tetrahydrofuran gave an analytical sample, mp 159°–160.5° (dec). Ir (Nujol): 3.08 and 3.16 (NH), 6.21 and 6.29 (CO$_2$$^-$), broad 9 (COC), and 10.24 and 10.77 μ (oxetane). Nmr ((CD$_3$)$_2$SO): very broad peaks due to paramagnetic Cu$^{++}$.

Anal. Calcd for C$_{22}$H$_{40}$CuN$_2$O$_{10}$: C, 47.51; H, 7.25; N, 5.04; Cu, 11.43. Found: C, 47.64; H, 7.59; N, 4.95; Cu, 11.51

EXAMPLE 4

2,6,12,15,21-Pentaoxa-9,18-diazaspiro[3.18]docosane

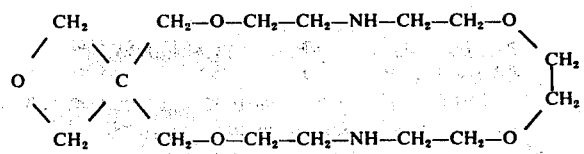

Preparation of the required 6,9-dioxa-3,12-diazatetradecane-1,14-diol was carried out as follows

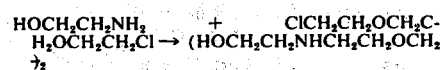

Two kilos (33 mol) of ethanolamine and 374 g (2.0 mol) of 1,8-dichloro-3,6-dioxaoctane were stirred and heated at 130° for one day. The mixture was cooled, 163 g (4.0 mol) of NaOH pellets were added, and the mixture was heated slowly with stirring to 100° and held there for 30 min. Most of the ethanolamine was then stripped off, 500 ml of tetrahydrofuran added, and the mixture filtered. Evaporation of the filtrate to 80° (0.5 mm) gave a concentrated product which was recrystallized from 1 l. of cold tetrahydrofuran to give 432.3 g (92%) of 6,9-dioxa-3,12-diazatetradecane-1,14-diol as an extremely hygroscopic solid, mp 49°–55°. An analytical sample was obtained by two recrystallizations from tetrahydrofuran, mp 53.5°–55°. Nmr ((CD$_3$)$_2$CO): 3.7–3.4 (multiplet with major peak at 3.59, 3, OCH$_2$), 3.23 (broad, OH + NH), and 2.85–2.6 ppm (multiplet, 2, NCH$_2$). Addition of D$_2$O moved the active H peak to 4.17 ppm (singlet, 1, OH + NH).

Anal. Calcd for C$_{10}$H$_{24}$N$_2$O$_4$: C, 50.83; H, 10.24; N, 11.86. Found: C, 51.22; H, 10.15; N, 11.67.

A solution of 202 g (0.855 mol) of 6,9-dioxa-3,12-diazatetradecane-1,14-diol, 132.8 g (0.855 mol) of 3,3-bis(chloromethyl)oxetane, and 191.5 g (1.71 mole) of potassium t-butoxide in 2.35 l. t-butanol was stirred and refluxed under N$_2$ for 5 days, cooled and filtered. The filtrate was concentrated to 50° (0.5 mm) and the residual oil extracted continuously with pentane for 4 days. Concentration of the extracts gave 198.4 g (71%) of a crude thick yellow oil. This product could not be purified by distillation, but nmr and ir indicated it to be 2,6,12,15,21-pentaoxa-9,18-diazaspiro[3.18]docosane. The structure was confirmed by isolation of the 1:1 complex with NaSCN in high yield as follows.

A solution in acetone (15 ml) of 3.18 g (0.01 mole of crude product and 0.81 g (0.01 mol) of NaSCN was evaporated to a volume of 10 ml and 5 ml of ether added. The cloudy solution was seeded with previously prepared complex and on standing gave 3.20 g (80%) of 1:1 complex, mp 147°–150°. Recrystallization from a small amount of acetone gave 2.63 g of complex, mp 151°–153.5°, shown by mixed mp to be the same as authentic complex. An analytical sample of similarly prepared complex had mp 151°–153°. IR (Nujol): 2.97 and 3.04 (NH), 4.82 (SCN), 8.5–9.5 (COC), 10.03, 10.48 and 10.53 μ (oxetane). Nmr (CCD$_3$)$_2$CO): 4.36 (singlet, 2, oxetane CH$_2$), 3.90 (singlet, 2, CCH$_2$O), 3.75–3.5 with major singlet at 3.64 for OCH$_2$CH$_2$O (multiplet, 6, OCH$_2$), and 2.23 ppm (broad, 1, NH), with one branch of A$_2$B$_2$ at 173.5, 168, and 164 Hz (4, NCH$_2$).

Anal. Calcd for C$_{16}$H$_{30}$N$_3$NaO$_5$S: C, 48.11; H, 7.57; N, 10.52; Na, 5.75. Found: C, 47.76; H, 7.57; N, 10.60; Na, 5.65.

A 1:1 complex with NaI was similarly obtained as hygroscopic crystals, mp 143°–145°. IR (Nujol): 3.09 (NH), 8.5–9.5 (COC), 10.07 and 10.57 μ (oxetane). Nmr ((CD$_3$)$_2$CO): 4.38 (singlet, 2, oxetane CH$_2$), 3.95 (singlet, 2, C-CH$_2$O), 3.7–3.55 with major singlet at 3.67 (multiplet, 6, OCH$_2$), 3.0–2.7 (multiplet, 2, NCH$_2$), and 1.83 ppm (singlet shifted downfield by D$_2$O, 1, NH).

Anal. Calcd for C$_{15}$H$_{30}$N$_2$NaO$_5$I: C, 38.47; H, 6.46; N, 5.98; I, 27.10. Found: C, 38.36; H, 6.37; N, 5.77; I, 26.90.

a. Acid-Catalyzed Hydrolysis of 2,6,12,15,21-Pentaoxa-9,18-diazaspiro[3.18]docosane The oxetane ring in these macrocycles can be opened, by addition of water as well as of alcohols. For example, acid-catalysed hydrolysis of 2,6,12,15,21-pentaoxa-9,18-diazaspiro[3.18]docosane yields 12,12-bis(hydroxymethyl)-1,4,10,14-tetraoxa-7,17-diazacyclononadecane.

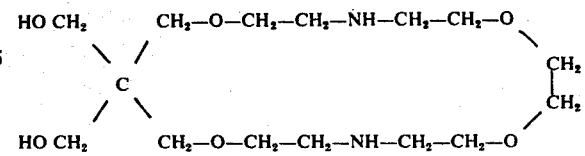

A solution of 99.1 g (0.31 mol) of crude 2,6,12,15,21-pentaoxa-9,18-diazaspiro[3.18]docosane and 39.2 (0.4 mol) of conc. $H_2SO_4$ in 2 l. of distilled water was refluxed for 3 days, treated with 32.0 g (0.80 mol) of NaOH pellets, and concentrated to low volume. Then 2 l. of xylene was added and distillation continued until the head temperature was 138°. The hot xylene was decanted and the residue was extracted with 2 × 500 ml hot xylene. Evaporation of the xylene extracts to 50° (0.5 mm) yielded 69.5 g (67%) of crude bis(hydroxymethyl)-1,4,10,14-tetraoxa-7,17-diazacyclononadecane as indicated by the ir spectrum (loss of oxetane band and appearance of hydroxyl absorption). A previous attempt to distill the diol resulted in considerable loss of product, but fractions with bp 188°–200° (0.15 $\mu$) were obtained. A sharply melting 1:1 complex with NaSCN was obtained as follows:

A sample of crude bis(hydroxymethyl)-1,4,10,14-tetraoxa-7,17-diazacyclononadecane (3.4 g, 0.01 mol) and 0.81 g (0.01 mol) of NaSCN were dissolved in acetone and acetone evaporated to give a heavy oil. Addition of 10 ml of ether and scratching induced crystallization. Ether was decanted and the largely solidified residue was recrystallized from acetone to give 2.46 g (59%) of 1:1 complex, mp 137°–140°. An analytical sample was recrystallized from acetone, mp 141.5°–142.5°. Ir (Nujol): 2.98 (OH), 3.06 (NH), 4.88 (SCN), 8.7–9.5 $\mu$ (COC, COH). Nmr ((CD$_3$)$_2$SO): 3.6–3.3 (multiplet with major peaks at 3.53 and 3.36, 5, OC$\underline{H}_2$), 3.14 ppm (broad, 1, O$\underline{H}$ + N$\underline{H}$, shifted downfield by D$_2$O) with one branch of A$_2$B$_2$ at 165, 160, and 155.5 Hz (2, NC$\underline{H}_2$).

Anal. Calcd for C$_{16}$H$_{32}$N$_3$NaO$_6$S: C, 46.03; H, 7.73; N, 10.06; Na, 5.51. Found: C, 46.41; H, 7.81; N, 10.24; Na, 6.24.

b. Acylation of 2,6,12,15,21-Pentaoxa-9,18-diazaspiro-[3.18]docosane

The amine function in these macrocycles can be acylated as well as alkylated, as shown by the following addition of a bridge to the two nitrogen atoms in 2,6,12,15,21-pentaoxa-9,18-diazaspiro[3.18]docosane under conditions of high dilution.

Solutions of 31.8 g (~ 0.10 mol) of crude $\underline{4}$ in 200 ml of dry benzene and 17.1 g (0.10 mol) of diglycolyl dichloride in 210 ml of dry benzene were added dropwise and simultaneously to a vigorously stirred mixture of 50 ml of triethylamine and 1 l. of dry benzene. After addition was completed (3.5 hr), stirring was continued an additional 15 min, the mixture was filtered to remove polymer and amine salts, and the filtrate was evaporated to give 26.3 g of viscous residue. Crystallization from acetone gave 12.3 g (30%) of

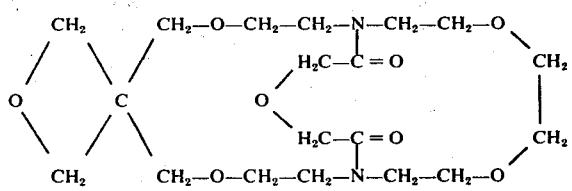

mp 178°–181°. An analytical sample was obtained from acetone, mp 180.5°–182°. Ir (Nujol): 6.03 (C=O), 8.6–9.6 (COC), 10.27 and 10.78 $\mu$ (oxetane). Nmr ((CD$_3$)$_2$SO): $^1$H 4.3–4.0 (multiplet, 1) and 3.7–3.2 (multiplet, 2).

Anal. Calcd for C$_{19}$H$_{32}$N$_2$O$_8$: C, 54.79; H, 7.75; N, 6.73; mol wt, 416. Found: C, 54.88; H, 7.92; N, 6.50; mol wt, 417. (ebul $\phi$H).

The embodiments of this invention in which an exclusive property or privilege is claimed are defined as follows:

1. A compound having the formula

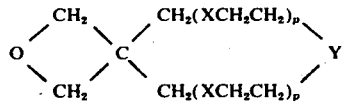

wherein:
Y is —OCH$_2$CH$_2$O—, —Z(CH$_2$CH$_2$O)$_2$—, or

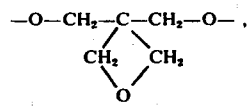

Z being —O—, —NH— or ≳NCH$_2$CH$_2$OH;
$p$ is 1 or 2; and
X is —O— or —NH—, with the proviso that the number of nitrogen atoms is from 1 to 3.

2. A compound of claim 1 wherein $p = 1$.
3. The compound of claim 1 named 2,9,12,15-tetraoxa-6,18-diazaspiro[3.15]nonadecane.
4. The compound of claim 1 named 2,6,9,15,18-pentaoxa-12-azaspiro[3.15]nonadecane.
5. The compound of claim 1 named 2,6,12,16,19-25-hexaoxa-9,22-diazadispiro[3.9.3.9]hexacosane.
6. The compound of claim 1 named 2,6,12,15,21-pentaoxa-9,18-diazaspiro[3.18]docosane.

* * * * *